(12) United States Patent
Spilker et al.

(10) Patent No.: US 11,685,712 B2
(45) Date of Patent: *Jun. 27, 2023

(54) SYNTHESIS OF MONOFUNCTIONAL THIURAM ACCELERATOR

(71) Applicant: The Goodyear Tire & Rubber Company, Akron, OH (US)

(72) Inventors: Thomas Franklin Spilker, Broadview Heights, OH (US); Ji Yang Jin, Akron, OH (US); Frank J. Feher, Copley, OH (US)

(73) Assignee: The Goodyear Tire & Rubber Company, Akron, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/894,651

(22) Filed: Aug. 24, 2022

(65) Prior Publication Data

US 2023/0029068 A1 Jan. 26, 2023

Related U.S. Application Data

(62) Division of application No. 17/117,537, filed on Dec. 10, 2020, now Pat. No. 11,465,968.

(60) Provisional application No. 62/955,323, filed on Dec. 30, 2019.

(51) Int. Cl.
*C07C 333/04* (2006.01)
*B01J 31/02* (2006.01)

(52) U.S. Cl.
CPC ......... *C07C 333/04* (2013.01); *B01J 31/0271* (2013.01)

(58) Field of Classification Search
None
See application file for complete search history.

(56) References Cited

U.S. PATENT DOCUMENTS 2,792,394 A 5/1957 Himel
7,217,834 B2 5/2007 Buding

FOREIGN PATENT DOCUMENTS

CN 106316905 B 1/2017

OTHER PUBLICATIONS

Corredor et al. (J. Chromatography A. 2009, 126, 43). (Year: 2009).
Extended European Search Report for European Patent Application No. EP20214489 dated May 21, 2021.

*Primary Examiner* — Sudhakar Katakam
*Assistant Examiner* — Jennifer C Sawyer
(74) *Attorney, Agent, or Firm* — Alvin T. Rockhill

(57) ABSTRACT

The present invention provides a route for synthesizing monofunctional thiuram compounds that is safe, environmentally friendly, and cost effective. This method specifically involves synthesizing a monofunctional thiuram by (1) reacting a tetraorganylthiuram disulfide with an organyl mercaptan to produce the monofunctional thiuram and a dithiocarbamate metal salt or a dithiocarbamate metalloid salt under basic conditions, (2) separating the monofunctional thiuram in an organic phase from the dithiocarbamate metal salt or the dithiocarbamate metalloid salt in an aqueous phase, and (3) recovering the monofunctional thiuram from the aqueous phase. The monofunctional thiuram compounds made in accordance with this invention are of particular value as accelerators for use in the vulcanization of rubber. The use of these monofunctional thiuram compounds as accelerators provides good cure rates and as well as good scorch safety.

20 Claims, No Drawings

SYNTHESIS OF MONOFUNCTIONAL THIURAM ACCELERATOR

This is a Divisional of United States patent application Ser. No. 17/117,537, filed on Dec. 10, 2020, which claims the benefit of United States Provisional Patent Application Ser. No. 62/955,323, filed on Dec. 30, 2019. The teachings of United States patent application Ser. No. 17/117,537 and United States Provisional Patent Application Ser. No. 62/955,323 are incorporated herein by reference in their entirety.

BACKGROUND OF THE INVENTION

Monofunctional thiuram compounds are useful as accelerators in the vulcanization (sulfur curing) of rubber and as a starting material in the synthesis of other useful compounds. Such monofunctional thiuram compounds include those of the structural formula:

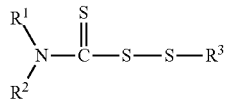

wherein $R^1$ and $R^2$ can be the same or different and represent organyl radicals, wherein $R^1$ and $R^2$ contain a total of at least 8 carbon atoms, and wherein $R^1$ and $R^2$ can join together to form a cyclic structure, and wherein $R^3$ represents an organyl radical containing at least 6 carbon atoms. The synthesis of monofunctional thiuram compounds of this general type is described in the prior art.

U.S. Pat. No. 2,792,394 discloses a process of reacting an alkyl sulfenyl halide in which the alkyl group contains from 1 to 12 carbon atoms and the halide is selected from the group consisting of chlorides, bromides, and iodides with an aqueous solution of a compound corresponding to the formula:

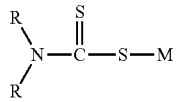

wherein

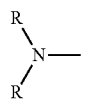

is a substituted amino group in which not more than one hydrogen is attached to the nitrogen atom, R and R' are selected from the group consisting of hydrogen, hydrocarbon radicals selected from the group consisting of alkyl, cycloalkyl, aryl, aralkyl radicals and radicals which in combination with nitrogen constitute saturated carbon-nitrogen, carbon-nitrogen-oxygen, and carbon-nitrogen-sulfur rings having not less than five and not more than six members of which at least four members are carbon atoms, and wherein M is a salt-forming cation, at a reaction temperature to produce alkyl sulfenyl dithiocarbamates.

U.S. Pat. No. 2,792,394 further explains that the products made by the method disclosed therein conform to the formula:

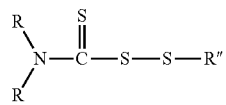

wherein

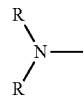

is a primary or secondary amino group in which either or both of R and R' may be alkyl, cycloalkyl, aryl, aralkyl hydrocarbon radicals or radicals which together with the nitrogen atom from a 5 or 6 membered saturated heterocyclic rings, at least 4 members being carbon atoms, such as piperidyl, morpholinyl, thiamorpholinyl, 2-methyl-thiomorpholinyl, pyrrolidyl, piperazinyl, pipecolinyl, etc, or in which either R or R' may be a hydrogen atom, and R" is an alkyl group.

U.S. Pat. No. 7,217,834 discloses a process for preparing salts of S-alkyl esters of thiosulphuric acid by reacting organic dihalides with thiosulphates in water. This prior art patent more specifically discloses a process for preparing the compounds of the formula $Me^1O_3S\ S\text{-}(CH_2)_n\text{-}S\ SO_3Me^2$ where $Me^1$ and $Me^2$ are the same or different and are each monovalent metal ions or ammonium ions and n is an integer from 2 to 8, characterized in that compounds of the formula $X\text{-}(CH_2)_n\text{-}X$, where X is halogen and wherein n is an integer from 2 to 8, are reacted with thiosulphate ions at a reaction temperature of 80° C. to 150° C. at a pH within the range of 3 to 9.8, with the reaction being carried out in water without addition of alcohols and/or glycols.

A better route for synthesizing monofunctional thiuram compounds is needed today. More specifically, such a synthesis route should be safe, environmentally friendly, and cost effective. More specifically such a synthesis route should avoid the use of chlorine species ($SO_2Cl_2$ or elemental chlorine). Such a synthesis route should also avoid the making RS-Cl intermediates which can be highly toxic and which are sometimes difficult to prepare from thiols.

SUMMARY OF THE INVENTION

The present invention provides a route for synthesizing monofunctional thiuram compounds that is safe, environmentally friendly, and cost effective. The method of this invention more specifically involves synthesizing a monofunctional thiuram by (1) reacting a tetraorganylthiuram disulfide with an organyl mercaptan to produce the monofunctional thiuram and a dithiocarbamate metal salt or a dithiocarbamate metalloid salt under basic conditions, (2) separating the monofunctional thiuram in an organic phase from the dithiocarbamate metal salt or the dithiocarbamate metalloid salt in an aqueous phase, and (3) recovering the monofunctional thiuram from the aqueous phase. The monofunctional thiuram compounds made in accordance with this invention are of particular value as accelerators for use in the vulcanization or rubber. The use of these monofunctional thiuram compounds as accelerators does not lead to high level of scorch and does not lead to cured rubbers that are highly susceptible to scorch.

Mixtures of monofunctional thiurams and the dithiocarbamate metal salts have been found to be highly useful as accelerator systems in the vulcanization of rubber formulations. Such mixtures can be easily and efficiently made in one specific embodiment of this invention. More specifically, this invention further reveals a method for synthesizing a monofunctional thiuram accelerator composition which comprises (1) reacting a tetraorganylthiuram disulfide with an organyl mercaptan to produce the monofunctional thiuram and a dithiocarbamate metal salt or a dithiocarbamate metalloid salt under basic conditions in a liquid solvent, and (2) recovering the monofunctional thiuram accelerator composition from the solvent as a mixture of the monofunctional thiuram and the dithiocarbamate metal salt or the dithiocarbamate metalloid salt. In this embodiment of the invention zinc hydroxide can be used to generate basic conditions and leads to the formation of zinc dithiocarbamate metal salts which are particularly useful in accelerator systems.

DETAILED DESCRIPTION OF THE INVENTION

The synthesis method of this invention involves reacting a tetraorganylthiuram disulfide with an organyl mercaptan under basic conditions to produce a monofunctional thiuram. Tetraorganylthiuram disulfides than can be employed in the synthesis of this invention are commercially available from a number of suppliers. For instance, Methyl Tuads® tetramethylthiuram disulfide, Ethyl Tuads® tetraethylthiuram disulfide, and Butyl Tuads® tetrabutylthiuram disulfide are sold by Vanderbilt Chemicals. Tetraalkylthiuram disulfide are also sold by Eastman Chemical. In any case, this reaction produces a dithiocarbamate metal salt as a reaction by-product as depicted below:

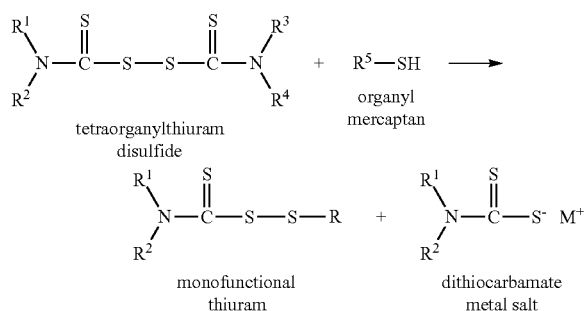

wherein $R^1$, $R^2$, $R^3$, and $R^4$ can be the same or different and represent organyl radicals. $R^1$, $R^2$, $R^3$, and $R^4$ normally contain from 1 to about 20 carbon atoms. Preferably $R^1$ and $R^2$ will contain a total of at least 8 carbon atoms and $R^1$ and $R^2$ can join together to form a cyclic structure. $R^3$ and $R^4$ also preferably contain a total of at least 8 carbon atoms and $R^3$ and R4 can join together to form a cyclic structure. $R^1$ and $R^2$ will typically contain a total of at least 10 carbon atoms. $R^1$ and $R^2$ will preferably contain a total of at least 12 carbon atoms and will more preferably contain a total of at least 14 carbon atoms. $R^3$ and $R^4$ will typically contain a total of at least 10 carbon atoms. $R^3$ and $R^4$ will preferably contain a total of at least 12 carbon atoms and will more preferably contain a total of at least 14 carbon atoms. $R^1$, $R^2$, $R^3$, and $R^4$ will preferably contain from 4 to 6 carbon atoms. For instance, it is preferred for $R^1$, $R^2$, $R^3$, and $R^4$ to be butyl group, pentyl groups, or hexyl groups with butyl groups being highly preferred. Accordingly, it is highly preferred for the tetraorganylthiuram disulfide to be tetrabutylthiuram disulfide. $R^5$ will normally represent an organyl radical containing at least 1 carbon atoms and will typically contain from 6 to about 20 carbon atoms. M represents a metal, such as sodium, potassium, manganese, zinc, and the like.

The reaction between the tetraorganylthiuram disulfide and the organyl mercaptan will typically be conducted in a polar organic solvent. The polar solvent may be a polar aliphatic solvent or polar aromatic solvent, such as an alcohol, a ketone, ester, acetate, glycol ethers, aprotic amide, aprotic sulfoxide, aprotic amine, or a halogenated hydrocarbon. Some representative examples of suitable polar organic solvents include tetrahydrofuran, dioxane, chloromethane, dichloromethane, chloroform, acetonitrile, methyl ethyl ketone, methyl isobutyl ketone, m-amyl acetate, ethylene glycol butyl ether-acetate, propylene glycol monomethyl ether acetate, xylene, toluene, benzene, n-methylpyrrolidone, ethanol, isopropanol, n-butanol, and n-propanol hexyl acetate, octyl acetate, propylene glycol monomethyl ether acetate, methyl propyl ketone, methyl isobutyl ketone, and methyl hexyl ketone, as well are various mixtures thereof. However, the polar organic solvent should be a liquid under the conditions that the reaction is conducted and should be inert with respect to reactants and reaction products.

The tetraorganylthiuram disulfide will normally be present in the polar organic solvent at a level which is within the range of about 5 weight percent to about 40 weight percent and will more typically be present at a level which is within the range of 10 weight percent to about 30 weight percent. It is typically preferred for the tetraorganylthiuram disulfide to be present in the polar organic solvent at a level which is within the range of 15 weight percent to 25 weight percent. The organyl mercaptan will be added at a slightly substoichiometric level with respect to the amount of the tetraorganylthiuram disulfide utilized in the reaction. In most cases, the molar ratio of the organyl mercaptan to the tetraorganylthiuram disulfide will be within the range of 15:20 to 19.9:20. The molar ratio of the organyl mercaptan to the tetraorganylthiuram disulfide will normally be within the range of 18:20 to 19.9:20, will typically be within the range of 19:20 to 19.8:20 and will more typically be within the range of 19.2:20 to 19.7:20.

A base which is strong enough to react with the organyl mercaptan will be added to attain and maintain basic conditions. Some representative examples of bases that can be used include sodium hydroxide, potassium hydroxide, calcium carbonate, sodium methoxide, zinc hydroxide and the like. The base will typically be utilized at a level which is sufficient to deprotonate the dithiocarbamic acid derivative formed in the reaction.

The reaction of this invention proceeds rapidly at ambient temperature. Accordingly, it will typically be conducted at ambient temperature. However, the method of this invention can be carried out over an extremely broad temperature range which is typically within the range of about −20° C. to about 100° C. It will more typically be conducted at a temperature which is within the range of 10° C. to 70° C. In most cases, the method of this invention will be conducted at a temperature which is within the range of 15° to 30° C. The reaction of this invention will normally be conducted under a dry inert gas atmosphere.

The monofunctional thiuram can be easily separated from the metal dithiocarbamate because it is soluble in organic solvents with the hydrogen dithiocarbamate being soluble in water. Accordingly, a phase separation can be used to recover the monofunctional thiuram in an aqueous phase from the metal dithiocarbamate in an aqueous phase.

The dithiocarbamate can optionally be oxidized to regenerate the tetraorganylthiuram disulfide which can subsequently be recycled for use in the first step of the process of this invention. The metal dithiocarbamate can be a metal salt, such as sodium dithiocarbamate, potassium dithiocarbamate, manganese dithiocarbamate, or zinc dithiocarbamate. Such metal salts, particularly zinc dithiocarbamate, can then also be utilized as accelerators in the vulcanization of rubber.

This invention is illustrated by the following examples that are merely for the purpose of illustration and are not to be regarded as limiting the scope of the invention or the manner in which it can be practiced. Unless specifically indicated otherwise, parts and percentages are given by weight.

Example 1

In this experiment 20 mmol (10.88 grams) of tetrabenzylthiuram disulfide (TBnTD) was added into 50 ml of degassed and anhydrous tetrahydrofuran (tetramethylene oxide) to make a tetrabenzylthiuram disulfide suspension. In another bottle 20 ml of tetrahydrofuran (THF), 3.65 ml (19.5 mmol) of 4-tert-butylbenzyl mercaptan (4-tert-butylbenzylthiol), and 4.35 ml (19.5 mmol) of sodium methoxide (CH$_3$ONa) were mixed together to form a white slurry. Then, the 4-tert-butylbenzyl mercaptan/sodium methoxide slurry was added in a dropwisely manner to the tetrabenzylthiuram disulfide suspension over a period of 1 hour with the mixture being stirred and maintained at room temperature for another 1 hour period. The tetrahydrofuran solvent was then removed with a rotary evaporator and the residue was diluted with toluene and then washed with water to remove the sodium dibenzylthiocarbamate salt which was form as a reaction by-product. Then the organic phase was again dried with a rotary evaporator to recover the N,N-dibenzyl-4-tert-butylbenzylsulfenyl dithiocarbamate. This reaction resulted in the recovery of 9.01 grams of product and a yield of 95%. The monofunctional thiuram recovered had a purity of 97%. The reaction carried out in this experiment can be illustrated as follows:

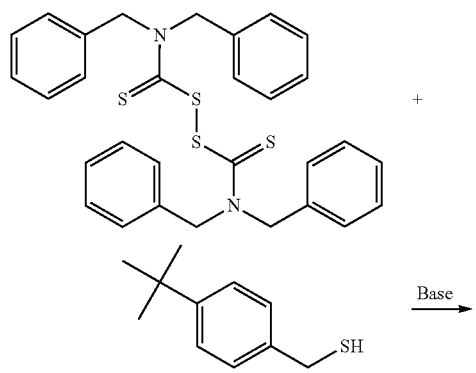

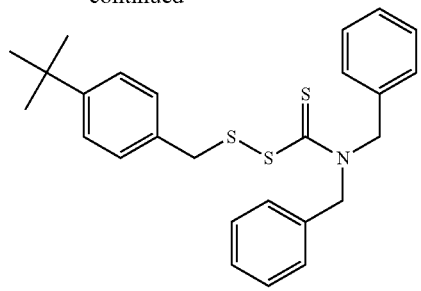

Example 2

In this experiment 10.88 grams (20 mmol) of tetrabenzylthiuram disulfide was mixed into 25 ml of anhydrous tetrahydrofuran (THF) to make a tetrabenzylthiuram disulfide suspension. In a separate vial 3.65 ml of 1,1-dimethylheptyl mercaptan was diluted with 10 ml of THF and 4.35 ml of a 25 weight percent solution of sodium methoxide (CH$_3$ONa) was added thereto. The thiol sodium salt solution which was produced was poured into the tetrabenzylthiuram disulfide suspension and the mixture turned clear immediately. The reaction was allowed to proceed while being stirred for an additional period of 1 hour. A rotary evaporator was then used to remove the THF solvent and the residue was diluted with toluene. The residue was then washed with water to remove the thiocarbamate salt. The organic phase was dried in the rotary evaporator and 8.05 grams of product was recovered. NMR showed it to have purity of 91%. The product yield of 87% was attained in this experiment. The reaction carried out in this experiment can be illustrated as follows:

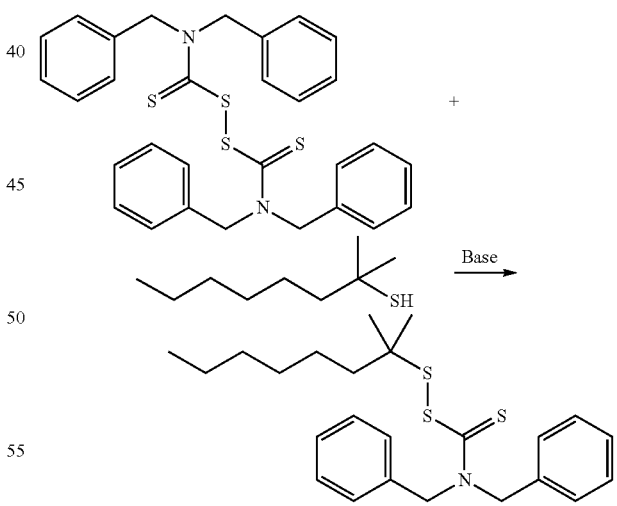

Example 3

In this experiment 4 mmol of tetrabenzylthiuram disulfide was suspended in 5 ml of THF to make a tetrabenzylthiuram disulfide suspension. In a separate mixing vessel containing 5 ml of THF 3.8 mmol of sodium methoxide (CH$_3$ONa) was mixed with 3.9 mmol of n-docecyl mercaptan to make a slurry containing 3.9 mmol of n-dodecanethiol-Na salt. It took significantly longer for the mixture to turn clear than it did in Example 1 when 4-tert-butylbenzyl mercaptan was used as a reactant. It was noted that some white solid remained after completion of the reaction. NMR showed that the product was a mixture of $C_{12}H_{25}$-SS-$C_{12}H_{25}$, residual tetrabenzylthiuram disulfide, and the desired thiuram product (N,N-di-benzyl-4-n-dodecanylbenzylsulfenyl dithiocarbamate). The reaction carried out in this experiment can be illustrated as follows:

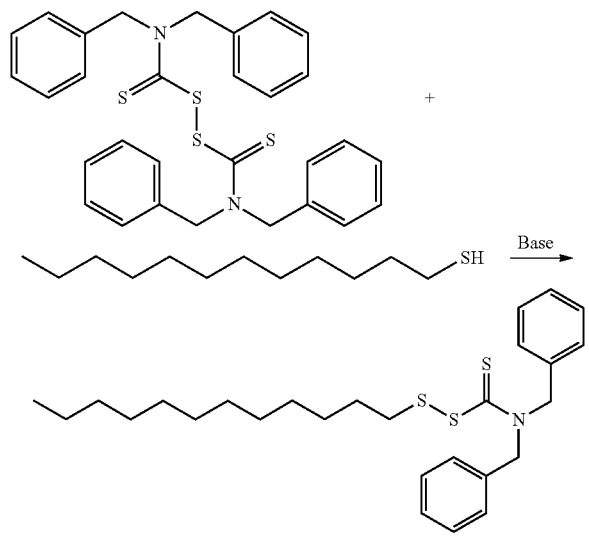

Example 4

In this experiment 23.93 (44 mmol) of tetrabenzylthiuram disulfide was suspended in 100 ml THF. A solution of the potassium salt of t-butylthiol was prepared by adding 4.72 ml of t-butylmercaptan (t-butylthiol) into a solution containing 2.49 grams (90%, 40 mmol) of potassium hydroxide (KOH) in 10 ml of methanol. The potassium t-butylthiol salt solution was then transferred into the tetrabenzylthiuram disulfide suspension with a cannula with stirring being maintained until the mixture turned clear. The reaction was allowed to continue with stirring being maintained for another 1 hour. The THF solvent was removed by the use of a rotary evaporator; the residue was diluted with hexane, and then washed with water to remove the thiocarbamate salt which was produced as a reaction by-product. The organic phase was then dried using the rotary evaporator with 12.23 grams of solid product (N,N-di-benzyl-tert-butylsulfenyl dithiocarbamate) being recovered. This resulted in a yield of 80.7%. The reaction carried out in this experiment can be illustrated as follows:

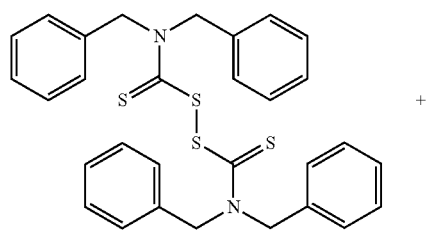

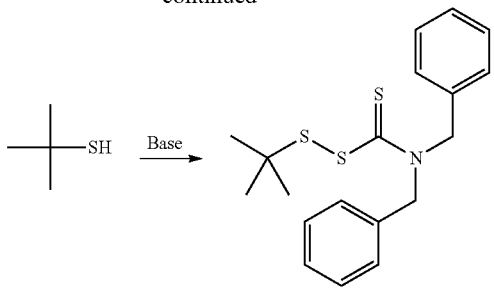

Example 5

In this procedure 0.55 ml (4.9 mmol) t-butylthiol was added into a vessel containing 3 ml of THF and subsequently 1.06 ml of sodium methoxide ($CH_3ONa$) solution (4.8 mmol) was added to make the sodium salt of t-butylthiol. In a separate vessel 1.20 grams of tetramethylthiuram disulfide (5 mmol) was suspended in 3 ml of THF and was then added in one portion to the sodium t-butylthiol salt solution. The solution turned clear immediately. The mixture was maintained under stirring for another 30 minutes to allow for the conversion of any remaining reactants. The solution was then concentrated under vacuum, diluted with 20 ml of toluene, and washed with 10% potassium carbonate ($K_2CO_3$) solution. The organic phase was dried and concentrated to provide 0.66 grams of N,N-di-methyl-tert-butylsulfenyl dithiocarbamate which was in the form of a white powder. This resulted in a yield of 63%. The reaction carried out in this experiment can be illustrated as follows:

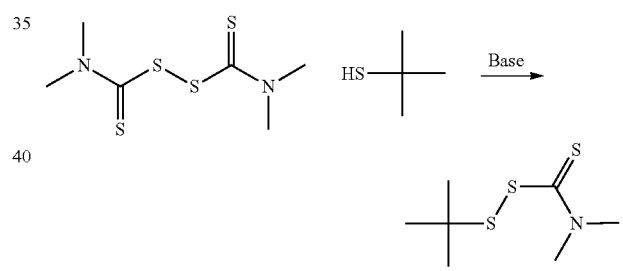

Example 6

In this experiment 8.16 grams (15 mmol) of tetrabenzylthiuram disulfide was suspended in 30 ml of anhydrous THF. In a separate vial 1.32 ml (14.4 mmol) of isopropyl mercaptan (isopropyl thiol) was diluted with 10 ml of THF and subsequently 3.15 ml of a 25 weight percent (13.8 mmol) sodium methoxide ($CH_3ONa$) solution was added to the vial to make the sodium salt of isopropyl mercaptan. The isopropyl mercaptan sodium salt solution was then poured into the tetrabenzylthiuram disulfide suspension and the mixture immediately turned clear. The mixture was maintained under stirring for another 40 minutes to allow for the conversion of any remaining reactants. The THF solvent was removed with a rotary evaporator and the residue was diluted with toluene and then wash with water to remove the thiocarbamate salt. The organic phase was dried and rotary evaporated again to recover 4.30 grams of N,N-di-benzyl-isopropylsulfenyl dithiocarbamate which appeared as a pale yellow solid. The reaction carried out in this experiment can be illustrated as follows:

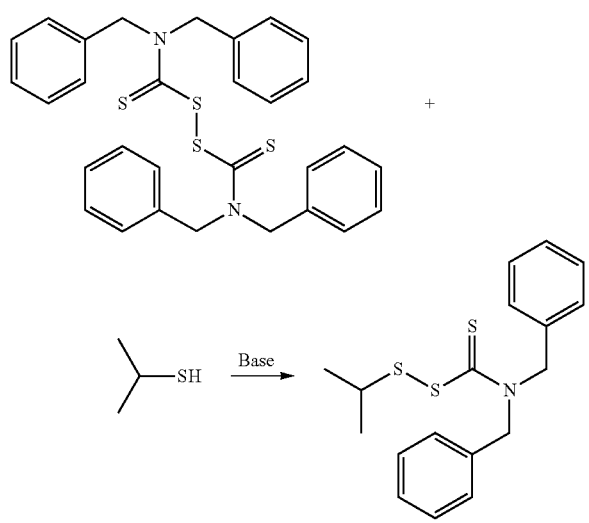

Example 7

In this experiment 2.72 grams (5 mmol) of tetrabenzylthiuram disulfide was suspended in 10 ml of anhydrous THF. In a separate vial 0.52 ml (4.8 mmol) of isobutyl thiol was diluted with 5 ml of THF and subsequently 1.06 ml (4.6 mmol) of a 25 weight percent solution of sodium methoxide (CH₃ONa) was added to make the sodium salt of isobutyl thiol. The isopropylthiol sodium salt solution was then poured into the tetrabenzylthiuram disulfide suspension which immediately turned clear. The mixture was maintained under stirring for another 40 minutes to allow for the conversion of any remaining reactants. The THF solvent was removed with a rotary evaporator and the residue was diluted with toluene. It was subsequently wash with water to remove the thiocarbamate salt which was produced as a by-product. The organic phase was again dried using the rotary evaporator with 1.34 grams of N,N-di-benzyl-isobutylylsulfenyl dithiocarbamate being recovered as a pale yellow solid. The resulted in a yield of 77%. The reaction carried out in this experiment can be illustrated as follows:

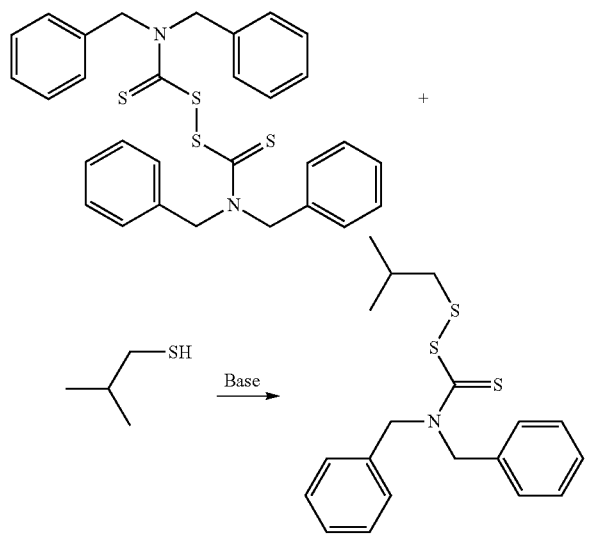

While certain representative embodiments and details have been shown for the purpose of illustrating the subject invention, it will be apparent to those skilled in this art that various changes and modifications can be made therein without departing from the scope of the subject invention.

What is claimed is:

1. A method for synthesizing a monofunctional thiuram accelerator composition which comprises (1) reacting a tetraorganylthiuram disulfide with an organyl mercaptan to produce the monofunctional thiuram and a dithiocarbamate metal salt or a dithiocarbamate metalloid salt under basic conditions in a liquid solvent, wherein the monofunctional thiuram is of the structural formula:

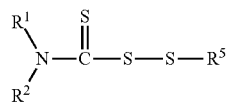

wherein $R^1$ and $R^2$ can be the same or different and represent organyl radicals, wherein $R^1$ and $R^2$ contain a total of at least 8 carbon atoms, and wherein $R^1$ and $R^2$ can join together to form a cyclic structure, and wherein $R^5$ represents an organyl radical containing at least 1 carbon atoms, and (2) recovering the monofunctional thiuram accelerator composition from the solvent as a mixture of the monofunctional thiuram and the dithiocarbamate metal salt or the dithiocarbamate metalloid salt.

2. The method of claim 1 which further comprises oxidizing the metal dithiocarbamate or metalloid dithiocarbamate to regenerate tetraorganylthiuram disulfide and recycling the regenerated tetraorganylthiuram disulfide to step (1).

3. The method of claim 1 wherein the tetraorganylthiuram disulfide is of the structural formula:

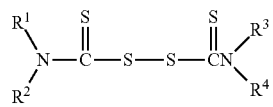

wherein $R^1$, $R^2$, $R^3$, and $R^4$ can be the same or different and represent organyl radicals, wherein $R^1$ and $R^2$ contain a total of at least 8 carbon atoms, wherein $R^1$ and $R^2$ can join together to form a cyclic structure, wherein $R^3$ and $R^4$ contain a total of at least 8 carbon atoms, and wherein $R^3$ and $R^4$ can join together to form a cyclic structure.

4. The method of claim 1 wherein $R^5$ contains from 6 to about 20 carbon atoms.

5. The method of claim 3 wherein $R^1$ and $R^2$ contain a total of at least 10 carbon atoms.

6. The method of claim 3 wherein $R^1$ and $R^2$ contain a total of at least 12 carbon atoms.

7. The method of claim 3 wherein $R^1$ and $R^2$ contain a total of at least 14 carbon atoms.

8. The method of claim 1 wherein the tetraorganylthiuram disulfide is tetrabenzylthiuram disulfide.

9. The method of claim 1 wherein the tetraorganylthiuram disulfide is tetrabutylthiuram disulfide.

10. The method of claim 1 wherein the dithiocarbamate metal salt or the dithiocarbamate metalloid salt is selected from the group consisting of sodium dithiocarbamate, calcium dithiocarbamate, potassium dithiocarbamate, magnesium dithiocarbamate, and zinc dithiocarbamate.

11. The method of claim 1 wherein the dithiocarbamate metal salt or the dithiocarbamate metalloid salt is a zinc dithiocarbamate salt.

12. The method of claim 1 wherein the tetraorganylthiuram disulfide is reacted with the organyl mercaptan in the presence of a zinc compound.

13. The method of claim 12 wherein the zinc compound is the anion of the conjugate base of an acid with a $pK_a$ greater than that of the dithiocarbamic acid derivative formed by the reaction of said method.

14. The method of claim 1 wherein the tetraorganylthiuram disulfide is reacted with the organyl mercaptan in a polar organic solvent.

15. The method of claim 1 wherein the polar organic solvent is selected from the group consisting of alcohols, ketones, esters, acetate, glycol ethers, aprotic amides, aprotic sulfoxides, aprotic amines, and halogenated hydrocarbons.

16. The method of claim 1 wherein the polar organic solvent is in the liquid state under the conditions at which the tetraorganylthiuram disulfide is reacted with the organyl mercaptan.

17. The method of claim 1 wherein the polar organic solvent is selected from the group consisting of tetrahydrofuran, dioxane, chloromethane, dichloromethane, chloroform, acetonitrile, methyl ethyl ketone, methyl isobutyl ketone, m-amyl acetate, ethylene glycol butyl ether-acetate, propylene glycol monomethyl ether acetate, xylene, toluene, benzene, n-methylpyrrolidone, ethanol, isopropanol, n-butanol, and n-propanol hexyl acetate, octyl acetate, propylene glycol monomethyl ether acetate, methyl propyl ketone, methyl isobutyl ketone, and methyl hexyl ketone.

18. The method of claim 1 wherein the polar organic solvent is tetrahydrofuran.

19. The method of claim 1 wherein the tetraorganylthiuram disulfide is reacted with the organyl mercaptan at a temperature which is within the range of 10° C. to 70° C.

20. The method of claim 1 wherein the tetraorganylthiuram disulfide is reacted with the organyl mercaptan at a temperature which is within the range of 15° to 30° C.

* * * * *